US011643646B2

(12) United States Patent
Chiu

(10) Patent No.: US 11,643,646 B2
(45) Date of Patent: May 9, 2023

(54) METHOD FOR ISOLATING AND PURIFYING NUCLEIC ACIDS USING A SOLID-LIQUID PHASE SYSTEM

(71) Applicant: Phase Scientific International, Ltd., Hong Kong (CN)

(72) Inventor: Yin To Chiu, Hong Kong (CN)

(73) Assignee: PHASE SCIENTIFIC INTERNATIONAL, LTD., Hong Kong (CN)

( * ) Notice: Subject to any disclaimer, the term of this patent is extended or adjusted under 35 U.S.C. 154(b) by 49 days.

(21) Appl. No.: 16/961,246

(22) PCT Filed: Jan. 18, 2019

(86) PCT No.: PCT/US2019/014330
§ 371 (c)(1),
(2) Date: Jul. 9, 2020

(87) PCT Pub. No.: WO2019/144030
PCT Pub. Date: Jul. 25, 2019

(65) Prior Publication Data
US 2021/0079376 A1 Mar. 18, 2021

Related U.S. Application Data

(60) Provisional application No. 62/619,274, filed on Jan. 19, 2018.

(51) Int. Cl.
*C12N 15/10* (2006.01)

(52) U.S. Cl.
CPC .............................. *C12N 15/1006* (2013.01)

(58) Field of Classification Search
CPC ................................................ C12N 15/1006
USPC ....................................................... 536/25.4
See application file for complete search history.

(56) References Cited

U.S. PATENT DOCUMENTS

| | | | |
|---|---|---|---|
| 6,132,763 A | 10/2000 | Fisher | |
| 6,399,385 B1 | 6/2002 | Croyle et al. | |
| 7,626,017 B2 | 12/2009 | Laugharn, Jr. et al. | |
| 7,666,583 B2 | 2/2010 | Mor et al. | |
| 7,803,405 B2 | 9/2010 | Keating et al. | |
| 9,823,247 B2 | 11/2017 | Kamei et al. | |
| 10,006,911 B2 | 6/2018 | Kamei et al. | |
| 10,359,423 B2 | 7/2019 | Kamei et al. | |
| 10,578,616 B2 | 3/2020 | Kamei et al. | |
| 11,287,426 B2 | 3/2022 | Kamei et al. | |
| 11,327,075 B2 | 5/2022 | Kamei et al. | |
| 2002/0042506 A1 | 4/2002 | Kristyanne et al. | |
| 2005/0077497 A1 | 4/2005 | Anderson | |
| 2006/0025579 A1 | 2/2006 | Riedl et al. | |
| 2006/0166349 A1 | 7/2006 | Kepka et al. | |
| 2007/0161000 A1* | 7/2007 | Van Alstine | B01D 15/34 |
| | | | 435/317.1 |
| 2008/0242825 A1 | 10/2008 | Devi et al. | |
| 2009/0192111 A1 | 7/2009 | Bader et al. | |
| 2009/0286966 A1 | 11/2009 | Christensen et al. | |
| 2010/0174052 A1 | 7/2010 | Hjorth et al. | |
| 2010/0179252 A1 | 7/2010 | Johansson et al. | |
| 2011/0257378 A1 | 10/2011 | Tran et al. | |
| 2011/0263040 A1 | 10/2011 | Jones | |
| 2013/0164825 A1 | 6/2013 | Christoffel et al. | |
| 2014/0221549 A1 | 8/2014 | Bodkhe et al. | |
| 2014/0227712 A1 | 8/2014 | Horlitz et al. | |
| 2014/0228549 A1 | 8/2014 | Schembecker et al. | |
| 2015/0253320 A1 | 9/2015 | Kamei et al. | |
| 2018/0100854 A1 | 4/2018 | Kamei et al. | |
| 2018/0259521 A1 | 9/2018 | Kamei et al. | |
| 2019/0033308 A1 | 1/2019 | Kamei et al. | |
| 2019/0187140 A1 | 6/2019 | Kamei et al. | |
| 2019/0250156 A1 | 8/2019 | Kamei et al. | |
| 2019/0391143 A1 | 12/2019 | Kamei et al. | |
| 2020/0150116 A1 | 5/2020 | Kamei et al. | |

(Continued)

FOREIGN PATENT DOCUMENTS

| | | |
|---|---|---|
| CN | 101679481 A | 3/2010 |
| CN | 102272144 A | 12/2011 |
| CN | 102421898 A | 4/2012 |

(Continued)

OTHER PUBLICATIONS

Ziegler YS, et al. (2014) Plasma membrane proteomics of human breast cancer cell lines identifies potential targets for breast cancer diagnosis and treatment. PLoS One. 9(7):e102341.

Schindler J, et al. (2008) Aqueous polymer two-phase systems for the proteomic analysis of plasma membranes from minute brain samples. J Proteome Res 7(1):432-442.

Spindler KL, et al. (2015) Circulating free DNA as biomarker and source for mutation detection in metastatic colorectal cancer. PLoS One.10(4):e0108247.

Riedl W, et al. (2008) Membrane-supported extraction of biomolecules with aqueous two-phase systems[J]. Desalination, 224(1-3): 160-167.

Frerix A, et al. (2005) Scalable recovery of plasmid DNA based on aqueous two-phase separation. Biotechnol Appl Biochem. 42(Pt 1):57-66.

(Continued)

*Primary Examiner* — Yih-Horng Shiao
(74) *Attorney, Agent, or Firm* — Eagle IP Limited

(57) ABSTRACT

The present invention provides a method and a system for the isolation and purification of nucleic acids from nucleic acid-containing material using a modified porous material containing cationic groups in a solid-liquid phase system. In some embodiments, the present invention is capable of obtaining nucleic acids with sufficient purity and quantity in a relatively simple way to enable accurate subsequent analysis or processing. In some embodiments, the liquid phase comprises an aqueous two-phase system (ATPS), comprising a first phase and a second phase, and the solid phase comprises a porous material, wherein the two phases travel through the porous material. In some embodiments, the nucleic acids enter the pores of the porous material and subsequently travel through the porous material while preferentially partitioning into one of the phases.

28 Claims, 1 Drawing Sheet

(56) References Cited

U.S. PATENT DOCUMENTS

| | | | |
|---|---|---|---|
| 2020/0284791 A1 | 9/2020 | Kamei et al. | |
| 2022/0252598 A1 | 8/2022 | Kamei et al. | |

FOREIGN PATENT DOCUMENTS

| | | | |
|---|---|---|---|
| CN | 106662582 A | 5/2017 | |
| CN | 110003323 A | 7/2019 | |
| EP | 0268946 A2 | 6/1988 | |
| JP | 2000245460 A | 9/2000 | |
| JP | 2002537106 A | 11/2002 | |
| JP | 2007525222 A | 9/2007 | |
| JP | 2017513015 A | 5/2017 | |
| WO | 0050161 A1 | 8/2000 | |
| WO | 2002057289 A1 | 7/2002 | |
| WO | 2011159537 A2 | 12/2011 | |
| WO | 2014128129 A1 | 8/2014 | |
| WO | 2015134938 A1 | 9/2015 | |
| WO | 2016155888 A1 | 10/2016 | |
| WO | 2017041030 A1 | 3/2017 | |
| WO | 2017214315 A1 | 12/2017 | |
| WO | 2018039139 A1 | 3/2018 | |
| WO | 2018183454 A1 | 10/2018 | |
| WO | 2018183465 A1 | 10/2018 | |
| WO | 2018222972 A1 | 12/2018 | |
| WO | 2019046553 A1 | 3/2019 | |
| WO | 2019046563 A1 | 3/2019 | |
| WO | 2019055926 A2 | 3/2019 | |
| WO | 2019118712 A1 | 6/2019 | |
| WO | 2019143895 A1 | 7/2019 | |
| WO | 2019143943 A2 | 7/2019 | |
| WO | 2019144016 A1 | 7/2019 | |
| WO | 2019144030 A1 | 7/2019 | |

OTHER PUBLICATIONS

Crucho Cic, et al. (2017) Polymeric nanoparticles: A study on the preparation variables and characterization methods. Mater Sci Eng C Mater Biol Appl. 80:771-784.

Shin H, et al. (2015) High-yield isolation of extracellular vesicles using aqueous two-phase system. Sci Rep. 5:13103.

Zeringer E, et al. (2015) Strategies for isolation of exosomes. Cold Spring Harb Protoc. (4):319-323.

Iqbal M, et al. (2016) Aqueous two-phase system (ATPS): an overview and advances in its applications. Biol Proced Online. 18:18.

Zhou et al. (2015) Nanoparticle Vesicles with Controllable Surface Topographies through Block Copolymer-Mediated Self-Assembly of Silica Nanospheres, Langmuir, vol. 31(48), 11 pp. 13214-13220.

Bashir et al. (2016) Controlled-release of Bacillus thurigiensis formulations encapsulated in light-resistant colloidosomal microcapsules for the management of lepidopteran pests of Brassica* crops, PEERJ., vol. 4(e2524). pp. 1-14.

Sigma-Aldrich "Poly(ethylene glycol) octyl ether" Retrieved from the Internet <URL:https://www.google.com/search?q=poly%28ethylene+glycol%29+octyl+ether&source=Int&tbs=cdr%3A1%2Ccd_min%3A%2Ccd_max%3A1%2F18%2F2018&tbm=> <URL https://www.sigmaaldrich.com/catalog/product/sigma/40530?lang=en®ion=US> [retrieved on Jun. 16, 2020].

Frank Luechau, et al., Partition of plasmid DNA in polymer-salt aqueous two-phase systems, Separation and Purification Technology, Apr. 20, 2009, pp. 397-404, vol. 66, No. 2, Elsevier Science, Amsterdam, NL.

Vijayaragavan K. Saagar et al., Separation of porcine parvovirus from bovine serum albumin using PEG-salt aqueous two-phase system, Journal of Chromatography B, Sep. 1, 2014, pp. 118-126, vol. 967, NL.

Erik Jue et al., Using an aqueous two-phase polymer-salt system to rapidly concentrate viruses for improving the detection limit of the lateral-flow immunoassay: Concentrating Viruses in a Polymer-Salt System, Biotechnology and Bioengineering, Dec. 1, 2014, pp. 2499-2507, vol. 111, No. 12, US.

Paz Sean et al., A simplified SARS-CoV-2 detection protocol for research laboratories, PLoS One, Dec. 18, 2020, p. e0244271, vol. 15, No. 12.

Luechau, Frank; et al. (2009) Primary capture of high molecular weight nucleic acids using aqueous two-phase systems. Separation and purification technology, 66.1:202-207.

Nazer, Behzad; et al. (2017) Plasmid DNA affinity partitioning using polyethylene glycol-sodium sulfate aqueous two-phase systems. Journal of Chromatography B, 1044: 112-119.

Sorber L, et al. (2017) A Comparison of Cell-Free DNA Isolation Kits: Isolation and Quantification of Cell-Free DNA in Plasma. J Mol Diagn. Jan;19(1):162-168.

Ricky Y. T. Chiu, et al., An Aqueous Two-Phase System for the Concentration and Extraction of Proteins from the Interface for Detection Using the Lateral-Flow Immunoassay, PLoS One, Nov. 10, 2015, 1-14, PLoS, California, US.

K. Jessie, et al., Protein Precipitation Method for Salivary Proteinsand Rehydration Buffer for Two-Dimensional Electrophoresis, Biotechnology, 2008, 686-693, 7 (4), Asian Network for Scientific Information.

Richard J. Wicks, et al., The extraction and purification of DNA labelled with [methyl-3 H]thymidine in aquatic bacterial production studies, Journal of Plankton Research, 1987, 1159-1166, vol. 9 No. 6, IRL Press Limited, Oxford, England.

Donald C Rio, et al., Purification of RNA by SDS solubilization and phenol extraction, Cold Spring Harb Protoc, Jun. 2010, 1-4, vol. 2010 Issue 6, Cold Spring Harbor Laboratory Press, NY, USA.

Zsolt Czimmerer, et al., A Versatile Method to Design Stem-Loop Primer-Based Quantitative PCR Assays for Detecting Small Regulatory RNA Molecules, PLoS One, Jan. 31, 2013, 1-10, vol. 8 Issue 1, PLoS, California, US.

Steven B. Zimmerman and Lizabeth D. Murphy, Excluded Volume Effects on the Partition of Single- and Double-Stranded Oligodeoxynucleotides Between Two Liquid Phases, Biopolymers, Oct. 1992, 1365-1373, vol. 32, Issue 10, John Wiley & Sons, Inc.

Steven B. Zimmerman and Stefan O. Trach, Excluded Volume Effects on the Partition of Macromolecules Between Two Liquid Phases, Biopolymers, 1990, 703-718, vol. 30, Issue 7-8, John Wiley & Sons, Inc.

T.Matos, et. al., Isolation of PCR DNA fragments using aqueous two-phase systems, Separation and Purification Technology, Feb. 10, 2014, 144-148, vol. 122, Elsevier B V.

Andreas Frerix, et. al., Exploitation of the Coil-Globule Plasmid DNA Transition Induced by Small Changes in Temperature, pH Salt, and Poly(ethylene glycol) Compositions for Directed Partitioning in Aqueous Two-Phase Systems, Langmuir, Mar. 25, 2006, 4282-4290, vol. 22 Issue 9, American Chemical Society.

Wu et al., "Factors Affecting Aqueous Two-Phase Extraction", Biopharmaceutical Technology (Fourth Edition), Aug. 2015, p. 122-126, China medicine science and technology press.

"Silicone Polyethers—Silsurf", Retrieved from the internet <URL: https://www.siltech.com/products/silicone-polyethers-silsurf/#:~:text=Silicone%20polyethers%2C%20or%20silicone%20surfactants,specific%20properties%20of%20a%20product>. [retrieved on Feb. 17, 2023].

* cited by examiner

METHOD FOR ISOLATING AND PURIFYING NUCLEIC ACIDS USING A SOLID-LIQUID PHASE SYSTEM

CROSS-REFERENCE TO RELATED APPLICATIONS

This application claims the benefit of U.S. Provisional Application No. 62/619,274, filed Jan. 19, 2018. The entire contents and disclosures of the preceding application are incorporated by reference into this application.

Throughout this application, various publications are cited. The disclosures of these publications in their entireties are hereby incorporated by reference into this application to more fully describe the state of the art to which this invention pertains.

FIELD OF THE INVENTION

The present invention relates to a method for isolating and purifying nucleic acids from a nucleic acid-containing material. In some embodiments, the method comprises using a modified porous material containing a cationic group or groups in a solid-liquid phase system. The modified porous material is useful to increase concentration of the target nucleic acids significantly by effectively capturing and holding the nucleic acids.

BACKGROUND OF THE INVENTION

Isolation and purification of high-quality nucleic acids are critical steps in many biotechnological applications. Performance of many analytical assays which involve testing of nucleic acids present in a particular medium largely depends on the purity and quantity of the target nucleic acids in the sample (e.g. blood or buccal cells). Results may be less reliable if the quantity or concentration of the target nucleic acids is too low in the sample or there are interfering molecules, such as non-target nucleic acids, other macromolecules, such as proteins, or small molecules, such as salts and detergents, present in considerable or minor amount in the sample. Therefore, separation of high purity and high quantity nucleic acids from other components in the original sample is critical to ensure high quality analysis of the nucleic acids.

Some ion exchange membranes (for example, those disclosed in U.S. Pat. Nos. 4,473,474 and 4,601,828) have been developed that possess increased affinity or binding capacity for biomolecules. However, modifications are only limited to the surface of the membrane. To date, there is no report on modifying the pores and/or capillary systems inside porous membranes to enhance the affinity or binding capacity.

U.S. Pat. No. 6,780,327 discloses a cationic charged membrane. The membrane comprises a hydrophilic substrate and a crosslinked coating to fix the positive charge to the membrane. However, preparation of such membranes involves complex chemistries and high process costs. Controlling the chemistry of some of the membranes, e.g., the degree of crosslinking, is relatively difficult and labor intensive.

Current methods for extraction and purification of nucleic acids from biological samples are usually time consuming, tedious, costly, and involve the use of hazardous organic solvents. In addition, the final quantity or concentration of nucleic acids collected does not always satisfy the requirements for downstream biotechnological applications and analysis. Hence, these methods may have limited applications in clinical laboratory or in industrial settings. Limitations of these methods may also include the lack of capacity to handle a large amount of samples and low compatibility with automation for rapid medical diagnosis.

To address some of the inadequacies in the art, the present invention provides a novel, simplified method and a system for nucleic acid isolation and purification that are highly compatible with various industrial, clinical and research uses.

SUMMARY OF THE INVENTION

In some embodiments, the present invention provides a solid-liquid phase system for rapid isolation and purification of nucleic acids from a nucleic acid-containing material. The system comprises a porous material as a solid phase and an aqueous two-phase system (ATPS) as a liquid phase. In some embodiments, the porous material comprises a surface and a plurality of pores, where the surface and pores comprise a plurality of cationic groups, and the ATPS comprises a first phase and a second phase.

In some embodiments, the present invention provides a method for isolation and purification of nucleic acids from a nucleic acid-containing material using a solid-liquid phase system comprising a modified porous material containing cationic groups. The modified porous material is able to increase concentration of the target nucleic acids significantly by effectively capturing and holding the target nucleic acids.

In some embodiments, the present invention is capable of isolating and purifying nucleic acids present in a biological material effectively and efficiently using modified porous material in which both the surface and the pore/capillary system are modified to contain cationic groups.

In some embodiments, the present invention is capable of isolating and purifying nucleic acids present in a biological material effectively and efficiently using modified porous material containing cationic groups. In some embodiments, the cationic groups may be aliphatic amines (primary, secondary or tertiary amines), such as dimethylamine, trimethylamine, octylamine, decylamine, dioctylamine and dodecylamine and combinations thereof. In some embodiments, the aliphatic amines comprise one to twelve carbon atoms. In some embodiments, cationic groups are aromatic amines, such as phenylenediamine, di(methylaminomethyl)phenol, tri(dimethylaminomethyl)phenol and diethylaniline or combinations thereof. In some embodiments, cationic groups are polyamines, such as spermidine, spermine, diethylenetriamine, triethylenetetramine, tetraethylenepentamine, pentaethylenehexamine, and tris(2-aminoethyl)amine and combinations thereof.

In some embodiments, the present invention provides a method for purifying nucleic acids from a nucleic acid-containing material, comprising the steps of:
a) obtaining a solid-liquid phase system comprising a solid phase and a liquid phase, wherein the solid phase comprises a porous material having a surface and a plurality of pores, wherein said surface and said pores contain a plurality of cationic groups and wherein the liquid phase comprises an aqueous two-phase system (ATPS) comprising a first phase and a second phase;
b) mixing the nucleic acid-containing material with the liquid phase, thereby obtaining a mixture; and
c) contacting the mixture obtained in step b) with the solid phase, wherein the nucleic acids are capable of binding to the solid phase and subsequently passing through the pores of the porous material resulting in purification of the nucleic acids.

As the surface and pore/capillary system of the porous material are modified to contain cationic groups carrying a positive charge, the porous material has a higher binding affinity for nucleic acids, which carry a negative charge. As a result, such porous material is more effective in capturing/holding nucleic acids, which may increase the collectable amount of nucleic acids compared to the amount that may be collected using unmodified porous materials. In some embodiments, the final concentration of nucleic acids collected may be increased from up to 10 to up to 1000 folds as compared to that in the original sample.

DETAILED DESCRIPTION OF THE INVENTION

Figure 1:
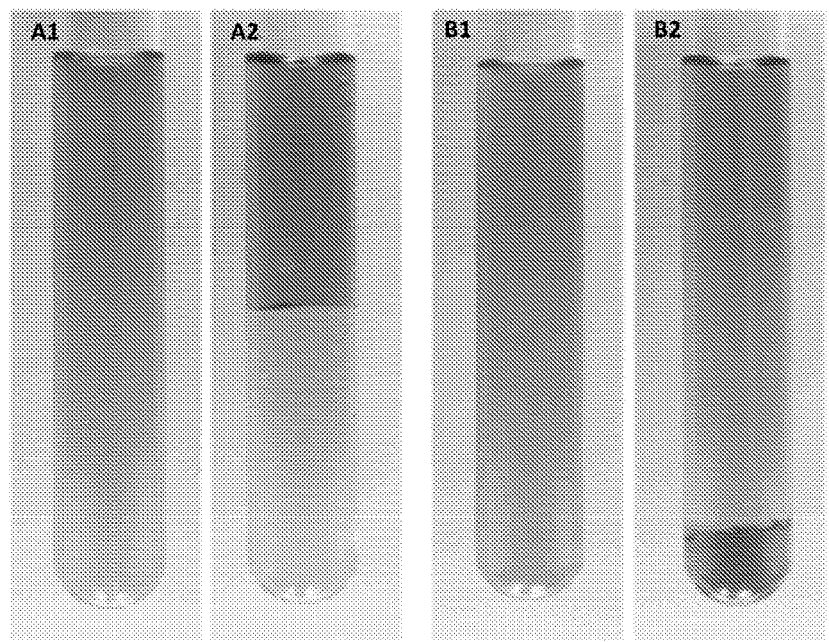
FIG. 1 shows a photograph of phase separation induced by the addition of polymer and salt to water. When certain salts and polymers are mixed in an aqueous solution, an aqueous two-phase system (ATPS) is formed and subsequently undergoes spontaneous phase separation. In the tubes depicted in Panels A1 and B1 the two phases are mixed forming a mixed phase, the salt-rich phase and the polymer-rich phase then gradually separate forming distinct layers, as shown in the tubes A2 and B2. The salt-rich phase in this example settles in the bottom portion of the tube while the polymer-rich phase is located above it. Different molecules, such as nucleic acids, may differentially distribute between the two phases due to their different properties. By changing the ratio of polymer to salt, the volume ratio of the two phases can be altered so that the target molecules are concentrated in the phase with a smaller volume. For example, 1:1 ratio of top phase to bottom phase is depicted in Panel A2, while 9:1 ratio is depicted in Panel B2. Panel B2 shows the target molecules (in this case, nanogold particles) concentrated in the bottom phase (the salt-rich phase) as is evident from the darker color resulting from the higher concentration of the target molecules in the bottom phase in Panel B2 compared to the bottom phase in Panel A2.

Unless indicated otherwise, the terms used herein, including technical and scientific terms, have the same meaning as usually understood by those skilled in the art to which the present invention pertains and detailed descriptions of well-known functions and constitutions that may obscure the gist of the present invention are omitted.

During the isolation of nucleic acids, various factors, such as the choice of materials of the isolating system, temperature, pressure, pH, chemical or enzymatic hydrolysis, as well as the presence of contaminants, may cause degradation of the nucleic acids and compromise their structural and functional integrity.

The present invention provides a solid-liquid phase system for purification of nucleic acids from nucleic acid-containing materials. The system comprises a porous material as a solid phase and an aqueous two-phase system (ATPS) as a liquid phase. In some embodiments, the porous material comprises a surface and a plurality of pores, where the surface and pores are modified to contain a plurality of cationic groups. In some embodiments, the ATPS comprises a first phase and a second phase.

In some embodiments, the methods provided herein are robust, inexpensive, simple, easy to handle, safe, user friendly and fast. In some embodiments, the present method allows to obtain the target nucleic acids of high purity and concentration in a simple way for downstream biotechnological applications and analysis. It ensures that the performance of the downstream applications using the isolated nucleic acids will not be affected by impurities in the original sample. Some embodiments do not require any additional power source, complex instrumentation or electronic hardware to operate and thus provide a fast and affordable means for rapid nucleic acid isolation and purification.

The liquid phase in the solid-liquid phase system provided in the present invention is an ATPS. An ATPS comprises two phases of different physicochemical properties. Different molecules, such as nucleic acids, differentially distribute between the two phases due to their different properties, thus making it possible to separate and concentrate the target molecules with minimal set up and human intervention. When an ATPS is applied to a porous material, the phases travel through the porous material at different rates. Thus, the target molecules may be concentrated in a certain portion of the porous material and subsequently collected therefrom.

In some embodiments, the solid phase of the present invention is comprised of a modified porous material containing cationic groups and is used in conjunction with the liquid phase comprising the ATPS described herein to isolate and purify the target nucleic acids from a nucleic acid-containing material. The target nucleic acids are able to enter the pores of the porous material and travel through the porous material while preferentially partitioning into one of the two phases of the ATPS. Finally, the target nucleic acids move to one end of the porous material and can be collected therefrom while non-target nucleic acids and non-nucleic acid materials are left in the other phase of the ATPS.

In some embodiments, an elution buffer or water may be used to elute the target nucleic acids from the porous materials. By adjusting the volume of the buffer or water used for eluting the target nucleic acids, concentration of the target nucleic acids can be manipulated. Smaller volume of the elution buffer or water will result in higher concentration of the target nucleic acids and larger volume will result in lower concentration. In some embodiments, the use of water or elution buffer is not necessary and the target nucleic acids may be collected by simply suctioning of the liquid phase of the ATPS that contains the target nucleic acids from the porous material.

Generally, a number of factors may determine the extent of partitioning of molecules, including nucleic acids, between the two phases of an ATPS, such as the nature of the molecule (e.g. size, charge, its respective affinity for the two phases), the nature of the ATPS (e.g. concentration and charge of the ATPS components, the interfacial tension between the two phases), the operating conditions (e.g.

temperature). Particular molecules that preferentially partition into one phase of a particular ATPS operated under one set of conditions may preferentially partition into the other phase if the conditions are changed. Relevant to this invention, the target nucleic acids are more likely to be retained in the top phase of an ATPS.

In some embodiments, both the surface and the pore/capillary system of the porous material are modified to contain cationic groups. The porous material containing cationic groups, which carry a positive charge, has a higher binding affinity for nucleic acids, which carry a negative charge, than a porous material that does not contain cationic groups. The modified porous material of the present invention may be used to increase concentration of the target nucleic acids significantly by effectively capturing and holding the target nucleic acids, even when their quantity in the original sample is low. The advantage of the current invention is that some embodiments allow to obtain higher purity and quantity of the target nucleic acids in a simpler way than can be obtained using conventional methods and the obtained nucleic acids are suitable for use in a variety of downstream biotechnological applications.

In some embodiments, the present invention provides a simple method to modify both the surface and the pore/capillary system of the porous material. The inventors unexpectedly found that a porous material can be modified to contain cationic amine groups by soaking the porous material in aqueous amine solution followed by vigorous stirring. In some embodiments, the cationic amine group is an aliphatic amine such as a primary, a secondary or a tertiary aliphatic amine or a combination thereof. Examples of aliphatic amines include, but are not limited to, dimethylamine, ethylenediamine, trimethylamine, octylamine, decylamine, dioctylamine or dodecylamine. In some embodiments, the aliphatic amine comprises one to twelve carbon atoms. In some embodiments, cationic amine groups are aromatic amines such as phenylene diamine, di(methylaminomethyl)phenol, tri(dimethylaminomethyl)phenol or diethylaniline. In some embodiments, cationic groups are polyamines, such as spermidine, spermine, diethylenetriamine, triethylenetetramine, tetraethylenepentamine, pentaethylenehexamine, and tris(2-aminoethyl)amine and combinations thereof. In some embodiments, the porous material is modified to contain aliphatic amines, aromatic amines and polyamines. In some embodiments, the porous material is modified to contain cationic groups other than aliphatic or aromatic amines or polyamines, including, but not limited to, ammonium, sulfonium or phosphonium.

In some embodiments, the present method simplifies the isolation of nucleic acids by simplifying or eliminating one or more steps in a typical purification process. In some embodiments, the use of organic solvents, such as alcohol, for extraction or washes is eliminated. In some embodiments, the present method permits simultaneous extraction of nucleic acids from a solution and separation of nucleic acids from impurities within a short period of time and produces nucleic acids of high purity which can be immediately used for further characterization and downstream processing.

Some embodiments of the present invention allow to obtain nucleic acids that can be used in a wide range of downstream applications, such as detection or analysis of the nucleic acids in forensic, diagnostic or therapeutic applications, and laboratory procedures, such as sequencing, amplification, reverse transcription, labeling, digestion, blotting procedures and the like. It is expected that some embodiments of the present invention are able to maintain the structural and functional integrity of the target nucleic acids thereby ensuring accurate performance of downstream characterization or processing of the isolated nucleic acids.

Because of the unique features described herein, some embodiments of the present invention can be used to isolate the target nucleic acids from small volume samples and samples containing very small amounts of the target nucleic acids conveniently and rapidly and without the use of external power source or complex instrumentation. Furthermore, the present method is readily adaptable to automation including high throughput screening systems.

In one embodiment, the present invention provides a method for rapid purification of one or more species of nucleic acids from a nucleic acid-containing material using a modified porous material containing cationic groups in a solid-liquid phase system, the method comprising:

a) mixing the nucleic acid-containing material with an ATPS comprising a first phase and a second phase, thereby obtaining a mixture; and b) contacting the mixture obtained from step a) with a solid phase comprising the modified porous material containing cationic groups, wherein one or more species of the nucleic acids in the mixture bind to the solid phase and subsequently pass through the pores within the modified porous material, thereby separating the nucleic acids from other molecules in the nucleic acid-containing material.

As the surface and/or the pore/capillary system of the present porous material is modified to contain cationic groups, which carry a positive charge, they have a higher binding affinity for nucleic acids, which carry a negative charge. As a result, the porous material modified in this way is more effective in capturing/holding the nucleic acids and significantly increases the final quantity of nucleic acids collected. In some embodiments, when the concentration of cations in the solution increases (for example as the solution is concentrated), some or all of the nucleic acids bound to the positively charged surface of the porous material are released and enter into the solution.

In some embodiments, the final concentration of nucleic acids obtained by the present invention is 10 to 1000 folds greater than that in the original sample. In some embodiments, nucleic acids captured by the present invention are extracted or eluted from the porous material using an appropriate buffer, thereby obtaining a purified sample. By measuring the concentration of nucleic acids in the original sample and that in the purified sample, the fold change in the concentration of the nucleic acids between the original sample and the purified sample can be estimated. In another embodiment, the fold change in concentration is estimated by calculating the concentrations of nucleic acids in the original sample and the purified sample based on their volume and the amount of nucleic acids contained therein.

In some embodiments, the nucleic acid isolated and/or purified using the present invention is DNA, such as genomic DNA, plasmid DNA, cell-free DNA or other DNA products of any length, size or configuration. In another embodiment, the nucleic acid isolated using the present invention is RNA, such as total RNA, messenger RNA, ribosomal RNA, cell-free RNA, miRNA, siRNA or other RNA products of any length, size or configuration. In another embodiment, the nucleic acids are peptide nucleic acids (PNA) of any length, size or configuration. In some embodiments, the nucleic acids isolated using the present invention is a combination of any of the nucleic acids specified above.

In some embodiments, the present invention can isolate nucleic acids having 20 to 1000 base pairs/nucleotides. In some embodiments, the nucleic acids are single-stranded, double-stranded or nicked.

The present invention can extract nucleic acids from nucleic acid-containing materials taken from biological or non-biological sources. In some embodiments, nucleic acid-containing materials include, but are not limited to, blood, plasma, serum, tissues, bacteria, viruses, RNA viruses, smear preparations, bacteria cultures, cell cultures, urine, saliva, fecal matter, and discharges such as tears, sputum, nasopharyngeal mucus, vaginal discharge, penile discharge, cell suspensions, adherent cells, polymerase chain reaction (PCR) mixtures and in vitro nucleic acid modification or reaction mixtures. In another embodiment, nucleic acid-containing materials comprise human, animal and/or plant material.

In some embodiments, the present invention is used to extract plasmid DNA from *Escherichia coli* or other microorganisms (e.g. bacteria and viruses) for subsequent cloning or sequencing or other molecular biology analysis. In some embodiments, the present invention is used to extract nucleic acids of any size (including short or long RNA or DNA, single-stranded or double-stranded) which originate from organisms, cells or derived from sequencing reactions or other comparable reactions. The isolated nucleic acid, especially DNA, from blood samples can be used for diagnosis of genetic diseases, diagnosis and monitoring of blood borne parasitic diseases, such as malaria, the determination of paternity and the monitoring of unusual cell populations in the blood as can occur in some neoplasms.

In some embodiments, contact between the nucleic acid-containing material and the solid phase comprising the modified porous material containing cationic groups is about 10 seconds to 5 minutes for the nucleic acids to adsorb on the solid phase. In another embodiment, the contact time is 15, 30 or 45 seconds. In another embodiment, the contact time is 1, 2, 3, 4 or 5 minutes. In various embodiments, the contact time chosen may depend on the type of the target nucleic acids to be extracted and the abundance of the target nucleic acids in the nucleic-acid containing material. The contact time can be further optimized by determining the quantity of nucleic acid adsorbed on the solid phase at different points in time. In this invention, since the binding affinity of nucleic acids for the modified porous material with cationic groups is significantly increased, the contact time can be significantly decreased without compromising the yield and purity of the nucleic acid in the final product.

In some embodiments, the present invention can isolate nucleic acids present in a solution at a concentration as low as 1 pg/mL. In some embodiments, the present invention can isolate nucleic acids from a relatively large volume of sample solution into a small volume as low as 1 μL.

Solid Phase

In some embodiments, the present invention provides a solid phase comprising a modified porous material which permits nucleic acids to pass through within its pore or capillary system. In some embodiments, the present invention does not require any chemical adsorption of the nucleic acids on the solid phase. Porous material may be made of any suitable porous material through which the target nucleic acids can pass including, but not limited to, various types of paper, polymer foams, cellulose foams, other types of foam, rayon fabric, cotton fabric, other types of fabric, wood, stones, ceramic, metal, agarose gel and carbon fibers. In some embodiments, materials including, but not limited to, fiberglass paper, cotton-based paper, single-layer matrix paper or polyolefin foam pad are used. Such materials may better preserve the structural and functional integrity of the nucleic acids.

In some embodiments, the porous material used in the present invention is paper made of non-cellulosic fiber. In contrast to conventional paper chromatography, the present invention uses a single mobile phase, i.e. an aqueous two-phase system (ATPS), which comprises two phases and undergoes phase separation as it travels through the solid phase (e.g. paper). The porous material may be commercially available or may be manufactured in-house.

In some embodiments, the present invention does not require any molecular probes or nanoparticles to capture the target nucleic acids in contrast to the conventional paper/membrane-based lateral flow assays (LFA), which employ thin layer paper, membranes, antibodies, molecular probes and/or gold nanoparticles to separate molecules in a mixture and to detect the target molecules based on the biochemical interaction between an antigen and an antibody or based on hybridization between a molecular probe and the target DNA. Rather, products obtained by the present invention can be used in any downstream processing or analysis including LFA analysis.

In some embodiments, a porous material is chosen such that small nucleic acids can freely enter the pores of the porous material while larger molecules such as large genomic DNA or non-nucleic acid macromolecules are excluded from the pores, thereby effectively separating these unwanted materials from the target nucleic acids. In some embodiments, the target nucleic acids from the nucleic acid-containing material can pass through the porous material by capillary action according to the isothermal-dynamic principles requiring no external power or additional equipment.

In the present invention, it is found unexpectedly that by choosing appropriate material for the solid phase and using the solid phase in conjunction with ATPS described herein, elution steps, which are normally required in conventional paper or membrane-based chromatography, may not be necessary for the isolation and purification of nucleic acids. The size of pores or capillary channels within the porous material can be readily chosen by one of ordinary skill in the art based on factors including the length, size, and/or configuration of the target nucleic acids, and may further depend on the size and configuration of non-target molecules present in the sample. In some embodiments, the pore diameter is in the range of 0.1-100 μm. In various embodiments, the pore size may be 20, 30, 40, 50, 60, 70, 80 or 90 μm. In some embodiments, the porous material is paper with pores 10-100 μm in diameter. In another embodiment, the porous material is paper with pores 4-5 μm in diameter.

To facilitate nucleic acid extraction or exclusion of non-target molecules, the solid phase may be treated with suitable materials to modify the physiochemical properties of the porous material. In some embodiments, reagents such as salt solutions, PEG solutions or Triton-X can be used to modify the microstructure of the porous materials. The porous material may be modified by attaching cationic groups to the porous materials permanently and/or transiently. For example, in addition to permanent cationic groups, transient positively charged moieties may be attached to the porous material to further enhance nucleic acid binding. In some embodiments where paper is used as the solid phase, positively charged moieties can be permanently or transiently attached to the fiber molecules of the paper.

In some embodiments, the porous material is coated with positively charged moieties. In some embodiments, the porous material is modified such that additional positively charged groups are formed (e.g. on the side facing the solution or within the pores) upon change of pH value of the solution in contact with the porous material. Thereby, nucleic acids, which are negatively charged, will be attracted to the cationic moieties on the surface of the porous material while impurities with positive charges will be expelled away.

In some embodiments, the present invention provides a method to modify both the surface and the pore/capillary system of the porous material comprising the step of soaking the porous material in amine aqueous solution followed by vigorous stirring. In some embodiments, fiber molecules of the paper are modified with an amine by the following preparation process: an amine is dissolved in an aqueous solution to obtain a 5 M amine aqueous solution. Porous paper is soaked in the 5 M amine aqueous solution followed by vigorous stirring at a speed of at least 700 rpm for an hour. The paper is kept in the solution at the temperature of 80° C. for 24 hours. Then the paper is taken out, washed twice with water and dried under compressed air. The concentration of the amine solution, time for mixing or stirring and other reaction conditions can be readily chosen by one of ordinary skill in the art based on various factors including the expected degree of coupling of cationic groups, the type and size of the porous material and so on. In general, a higher concentration of the amine solution or a longer period of time for mixing results in a higher degree of coupling of cationic groups to the porous material.

In some embodiments, amine used for modifying the porous material is an aliphatic amine, such as a primary, a secondary or a tertiary aliphatic amine or combinations thereof. Examples of aliphatic amines include, but are not limited to, dimethylamine, trimethylamine, trimethylamine, octylamine, decylamine, dioctulamine or dodecylamine. In some embodiments, the aliphatic amine comprises one to twelve carbon atoms. In some embodiments, the amine is an aromatic amine such as phenylene diamine, di(methylaminomethyl)phenol, tri (dimethylaminomethyl)phenol or diethylaniline. In some embodiments, cationic groups are polyamines, such as spermidine, spermine, diethylenetriamine, triethylenetetramine, tetraethylenepentamine, pentaethylenehexamine, and tris(2-aminoethyl)amine and combinations thereof. In some embodiments, aliphatic amines, aromatic amines and polyamines are used to modify the porous material. In some embodiments, one or more types of cationic groups other than amine groups are attached to the present porous material.

In some embodiments, the porous material is modified so as to reduce non-specific binding between the porous material and non-target molecules, such as proteins, in the solution. In various embodiments, the above modifications of the porous material can be done uniformly, randomly or confined to a specific region (or regions) of the porous material.

In some embodiments several layers of a porous material may be used. In other embodiments, only one layer of a porous material is used. The porous material used may be of any suitable dimension. In some embodiments, the porous material is rectangular in shape and is 0.5×4×0.083 cm in size. In some embodiments, the thickness of the porous material may be 0.5 mm to 5 mm. One of skill in the art would understand that the size of the porous material to be used in the present invention may be selected based on the size of the container in which the sample from which the target nucleic acids are to be isolated is contained, the volume of the sample and/or other factors.

In some embodiments, layers of fiber-containing paper or other porous materials or combinations thereof are formed into stacks. These stacks may be formed by stacking layers (or sheets) of material and cutting the resulting stacks to a suitable size. The stacks may be formed from two or more layers (or sheets) of porous material. In some embodiments, the stacks are formed from four layers of porous material. In some embodiments this porous material is fiber-containing paper. In some embodiments, the porous material is fiberglass paper. Stacks formed from fiber-containing paper are sometimes referred to herein as paper stacks. In some embodiments, the stacks are rectangles measuring 0.5 cm by 4 cm in size.

Liquid Phase

The liquid phase of the present invention is an aqueous two-phase system (ATPS) comprising a first phase and a second phase. In some embodiments, one of the phases of the ATPS comprises a micellar solution and the other phase comprises a polymer or polymers. In some embodiments, one phase of the ATPS comprises a micellar solution and the other phase comprises a salt or salts. In some embodiments, the micellar solution is a Triton-X solution. In some embodiments, one phase comprises a first polymer and the other phase comprises a second polymer. In some embodiments, the first and/or second polymer is selected from polyethylene glycol and dextran. In some embodiments, one phase comprises a polymer or polymers and the other phase comprises a salt or salts. In some embodiments, one phase comprises polyethylene glycol and the other phase comprises potassium phosphate. In some embodiments, one phase comprises a salt or salts and the other phase comprises a salt or salts. In some embodiments, one phase comprises a kosmotropic salt or salts and the other phase comprises a chaotropic salt or salts. In some embodiments, one phase comprises an alcohol or alcohols and the other phase comprises a salt or salts.

In the following sections, concentration of the ATPS components (e.g. polymers, salts, alcohols and others) is expressed as weight percent (w/w) (i.e., weight of the component divided by the total weight of the solution), or as molarity (M) (i.e. the number of moles of the component in one liter of the solution).

In some embodiments, the first and the second phase comprise a polymer or polymers.

Polymers that may be used in the present invention include, but are not limited to, polyalkylene glycols, such as hydrophobically modified polyalkylene glycols, poly(oxyalkylene)polymers, poly(oxyalkylene)copolymers, such as hydrophobically modified poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, and poly N-isopropylacrylamide and copolymers thereof. In some embodiments, polyethylene glycol, polypropylene glycol, or dextran may be used.

In some embodiments, the polymer concentration is in the range of about 0.01% to about 90% by weight of the total weight of the aqueous solution (w/w). In various embodiments, the polymer concentration may be about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, or about 1% w/w. In some embodiments, the polymer concentration may be about 1% w/w, about 2% w/w, about 3% w/w, about 4% w/w, about 5% w/w, about 6% w/w, about 7% w/w, about 8% w/w, about 9% w/w, about 10% w/w, about 1 1% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w.

Salts that may be used in the present invention include, but are not limited to, kosmotropic salts, chaotropic salts, inorganic salts containing cations, such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium, and anions, such as phosphates, sulphate, nitrate, chloride and hydrogen carbonate. In some embodiments, the salt is selected from the group consisting of sodium chloride, trisodium phosphate, sodium sulfate, potassium phosphate, potassium citrate, ammonium sulfate, sodium citrate, sodium acetate and combinations thereof. Other salts, e.g. ammonium acetate, may also be used.

In some embodiments, the total salt concentration is in the range of 0.001 mM to 100 mM. In various embodiments, the salt concentration may be about 0.001% to 90% w/w. In various embodiments, the salt concentration may be about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9%) w/w, about 0.95% w/w, or about 1% w/w. In some embodiments, the salt concentration may be about 1% w/w, about 2% w/w, about 3% w/w, about 4% w/w, about 5% w/w, about 6% w/w, about 7% w/w, about 8% w/w, about 9% w/w, about 10% w/w, about 1 1% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w.

A person skilled in the art will understand that when one of the phases of the ATPS comprises a polymer and another phase comprises a salt, the amount of salt needed to form an ATPS is influenced by molecular weight, concentration and physical status of the polymer.

In some embodiments, the first phase and/or the second phase in the liquid phase comprises a solvent that is immiscible with water. In some embodiments, the solvent is a non-polar organic solvent. In some embodiments, the solvent is an oil. In some embodiments, the solvent is selected from pentane, cyclopentane, benzene, 1,4-dioxane, diethyl ether, dichloromethane, chloroform, toluene and hexane.

In some embodiments, the first phase and/or second phase of the ATPS comprises a micellar solution. In some embodiments, the micellar solution comprises a nonionic surfactant or surfactants. In some embodiments, the micellar solution comprises a detergent or detergents. In some embodiments, the micellar solution comprises Triton-X. In some embodiments, the micellar solution comprises a polymer similar to Triton-X, such as Igepal CA-630 and Nonidet P-40. In some embodiments, the micellar solution consists essentially of Triton-X.

In some embodiments, the pH value of the first phase and/or second phase of the ATPS is 6.5-8.5. In some embodiments, the pH value of the first phase and/or second phase in the phase is 7.0.

In some embodiments, ratios of the first phase to the second phase are in the range of 1:1 to 1:1000. In some embodiments, the ratio of the first phase to the second phase is selected from a ratio of about 1:1, about 1:2, about 1:3, about 1:4, about 1:5, about 1:6, about 1:7, about 1:8, about 1:9, and about 1:10. In some embodiments the ratio of the first phase to the second phase is selected from a ratio of about 1:20, about 1:30, about 1:40, about 1:50, about 1:60, about 1:70, about 1:80, about 1:90, and about 1:100. In some embodiments the ratio of the first phase to the second phase is selected from a ratio of about 1:200, about 1:300, about 1:400, about 1:500, about 1:600, about 1:700, about 1:800, about 1:900, and about 1:1000.

In some embodiments, the ratio of the second phase to the first phase is selected from a ratio of about 1:1, about 1:2, about 1:3, about 1:4, about 1:5, about 1:6, about 1:7, about 1:8, about 1:9, and about 1:10. In some embodiments the ratio of the second phase to the first phase is selected from a ratio of about 1:20, about 1:30, about 1:40, about 1:50, about 1:60, about 1:70, about 1:80, about 1:90, and about 1:100. In some embodiments the ratio of the second phase to the first phase is selected from a ratio of about 1:200, about 1:300, about 1:400, about 1:500, about 1:600, about 1:700, about 1:800, about 1:900, and about 1:1000.

In some embodiments, an ATPS is prepared by mixing ATPS components, such as salts, polymers, alcohols and others as described above, in an aqueous solution. In some embodiments, an ATPS is prepared by mixing a first solution and a second solution containing different components of the ATPS. In other embodiments, the components of the first phase and the second phase are embedded in a modified porous material. When water or an aqueous solution, such an aqueous solution containing the target nucleic acids, flows through the modified porous materials, the ATPS components embedded in the material solubilize and an ATPS is formed. The resulting ATPS then undergoes phase separation.

ATPS components may be embedded in a modified porous material in a number of ways. Some of the ways are described below. In some embodiments, ATPS is dehydrated onto the porous material. In some embodiments, the porous material is inserted into an ATPS and then air dried. In some embodiments, the porous matrix is inserted into the premixed ATPS and then dried by hot air, lyophilization or supercritical drying. In some embodiments, the premixed ATPS components are sprayed onto the porous material and then dried by any of the above-mentioned drying methods or otherwise. In some embodiments, ATPS components of different types or concentrations are sprayed onto the same or different areas of the porous material and then dried. In some embodiments, where multiple layers of porous material are used, ATPS components of different types or concentrations are sprayed onto different layers of the porous material separately and then dried. In some embodiments, ATPS components of different types or concentrations are sprayed onto different areas of the porous material separately and then dried.

In various embodiments, the present invention can be used in combination with one or more processes or reagents for the purpose of washing and eluting the target nucleic acids retained in the porous material, or for post-isolation treatment of the retained nucleic acids.

In some embodiments, after contacting the nucleic acid-containing solution with the solid phase, a washing buffer is applied to the solid phase, once or multiple times, to wash off non-target molecules or impurities from the porous material. Washing buffers may comprise solutions of varying ionic strength and pH values and may contain additives, such as detergents. Examples of washing buffers include, but are not limited to, a solution of 20%-50% ethanol and 20%-50% isopropanol; a solution of about 0.1-4.0 M guanidine hydrochloride, solutions of detergents and up to about 80% ethanol or a solution of about 80% ethanol.

In some embodiments, the target nucleic acids enter the porous material of the solid phase and flow to one end of the porous material. In some embodiments, nucleic acids isolated by the present invention are eluted out of the porous material using appropriate elution buffers or deionized water. In some embodiments, isolated nucleic acids are not eluted but stored for future use in the porous material. For instance, after the isolation of nucleic acids using the present invention, the paper containing the target nucleic acids may be dried and stored. In some embodiments, nucleic acids retained on the porous material (e.g. paper) can be eluted for further analysis or treatment. Selection of the elution buffer may depend on the contemplated use of the purified nucleic acids. Examples of suitable elution buffers include, but are not limited to, Tris-EDTA (TE) buffer, aqua bidest and PCR buffer. In some embodiments, the purified nucleic acids on porous paper are eluted in a tube containing TE buffer (10 mM Tris-Cl, 1 mM EDTA solution with pH 7.5), and the purified nucleic acids are recovered in a relatively small volume, e.g., less than 100 µl.

Downstream applications of the purified nucleic acids include, but are not limited to, detection or analysis of the nucleic acids, forensic, diagnostic or therapeutic applications and laboratory procedures, such as sequencing, amplification (e.g. PCR, RT-PCR, real-time PCR, and real-time RT-PCR), reverse transcription, labeling, digestion, blotting procedures and the like.

In the present invention, the nucleic acid-containing materials in solution may be prepared from cells of human, plant, animal, viral or bacterial origin. For some applications it is necessary to separate the nucleic acids from non-nucleic acid materials (e.g., peptides, proteins, oligosaccharides, lignans, small molecule natural products and other materials typically of natural origin). It is expected that some embodiments of the present invention can effectively and efficiently separate the nucleic acids and non-nucleic acid materials and can obtain nucleic acid products of high yield and purity. Purity of DNA can be estimated by the ratio of absorbance values at 260 nm and 280 nm (A260/280) as described in Glasel J. (1995) Biotechniques. Table 2 shows the percentage of nucleic acids and proteins in a sample predicted according to the A260/280 ratio.

In some embodiments, the nucleic acids isolated by the present invention have a purity of at least 50%, 60%, 70%, 80%, 90%, 95%, 99% or more.

Accordingly, some embodiments of the present invention are suitable to remove at least 50%, 60%, 70%, 80%, 90%, 95%, 99% or more of non-nucleic acid materials in a nucleic acid-containing sample.

TABLE 2

Absorbance and Percentage of Nucleic Acids and Proteins

| $A_{260/280}$ | % nucleic acid | % protein |
| --- | --- | --- |
| 0.57 | 0 | 100 |
| 1.06 | 5 | 95 |
| 1.32 | 10 | 90 |
| 1.59 | 20 | 80 |
| 1.72 | 30 | 70 |
| 1.75 | 40 | 60 |
| 1.81 | 50 | 50 |
| 1.85 | 60 | 40 |
| 1.85 | 70 | 30 |
| 1.81 | 80 | 20 |
| 1.82 | 90 | 10 |
| 1.88 | 95 | 5 |
| 1.86 | 100 | 0 |

In some embodiments, the present invention provides a solid-liquid phase system for purification of nucleic acids from a nucleic acid-containing material, the system comprises a porous material and an aqueous two-phase system (ATPS), wherein the porous material comprises a surface and a plurality of pores, wherein the surface and the pores comprise a plurality of cationic groups, and the aqueous two-phase system comprises a first phase and a second phase.

In some embodiments of the present solid-liquid phase system, the plurality of cationic groups is selected from the group consisting of aliphatic amines, aromatic amines, polyamines and combinations thereof.

In some embodiments of the present solid-liquid phase system, the plurality of cationic groups is selected from the group consisting of dimethylamine, spermidine, spermine, trimethylamine, trimethylamine, octylamine, decylamine, dioctylamine and dodecylamine, phenylene diamine, di(methylaminomethyl)phenol, tri(dimethylaminomethyl)phenol, diethylaniline, spermidine, spermine, diethylenetriamine, triethylenetetramine, tetraethylenepentamine, pentaethylenehexamine, tris(2-aminoethyl)amine and combinations thereof.

In some embodiments of the present solid-liquid phase system, the porous material is paper, polymer, foam, fabric, wood, stone, ceramic, metal, agarose gel or carbon fiber.

In some embodiments of the present solid-liquid phase system, the porous material is fiberglass paper, cotton-based paper, single-layer matrix paper or polyolefin foam pad.

In some embodiments of the present solid-liquid phase system, the porous material has an average pore size in the range of 0.1 to 100 µm.

In some embodiments of the present solid-liquid phase system, the first phase and the second phase of the ATPS is independently selected from the group consisting of a polymer solution, a salt solution, a non-polar solution, a micellar solution and a polyelectrolyte solution. In some embodiments, the first phase is a polymer solution, a salt solution, a non-polar solution, a micellar solution or a polyelectrolyte solution. In some embodiments, the second phase is a polymer solution, a salt solution, a non-polar solution, a micellar solution or a polyelectrolyte solution.

In some embodiments of the present solid-liquid phase system, the volume of the first phase and the volume of the second phase of the ATPS are in a ratio of 1:1 to 1:1000.

In some embodiments of the present solid-liquid phase system, the nucleic acids to be purified have a size of about 20 to 1000 base pairs.

In some embodiments of the present solid-liquid phase system, the system can purify the target nucleic acids within 10 seconds to 5 minutes.

In some embodiments of the present solid-liquid phase system, the concentration of the target nucleic acids purified using the present solid-liquid phase system is 10 to 1000 folds higher than the concentration of the target nucleic acids in the nucleic acid-containing material.

In some embodiments of the present solid-liquid phase system, the nucleic acids to be purified are present in the nucleic acid-containing material at a concentration of 1 pg/mL or higher.

In some embodiments, the present invention provides a method for preparing a porous material comprising a plurality of cationic groups, the method comprises the steps of
(a) preparing an amine solution by dissolving an amine in a buffer;
(b) soaking the porous material in the amine solution obtained from step (a);
(c) washing the porous material obtained from step (b) with water; and
(d) drying the porous material obtained from step (c), thereby obtaining a porous material comprising a plurality of cationic groups.

In some embodiments of the present method, the amine of the step (a) is dimethylamine, spermidine, spermine, trimethylamine, trimethylamine, octylamine, decylamine, dioctylamine, dodecylamine, phenylene diamine, di(methylaminomethyl)phenol, tri(dimethylaminomethyl)phenol and diethylaniline or combinations thereof.

In some embodiments of the present method, the porous material is paper.

In some embodiments the present invention provides a method of using the solid-liquid phase system for rapid purification and concentration of nucleic acids from a nucleic acid-containing material.

In some embodiments, the present invention provides a method for purifying nucleic acids from a nucleic acid-containing material, the method comprises the steps of:
(a) obtaining a solid-liquid phase system comprising a solid phase and a liquid phase, wherein the solid phase comprises a porous material comprising a surface and a plurality of pores, the surface and the pores comprise a plurality of cationic groups, and wherein the liquid phase comprises an aqueous two-phase system (ATPS);
(b) mixing the nucleic acid-containing material with the liquid phase, thereby obtaining a mixture; and
(c) contacting the mixture obtained from step (b) with the solid phase,
wherein the nucleic acids are capable of binding to the solid phase and subsequently passing through the pores of the porous material, wherein the nucleic acids are concentrated on the porous material.

In some embodiments, the present method further comprises a step of eluting the nucleic acids from the porous material of the solid phase.

In some embodiments of the present method, the plurality of cationic groups is selected from the group consisting of aliphatic amines, aromatic amines, polyamines and combinations thereof.

In some embodiments of the present method, the plurality of cationic groups is selected from the group consisting of dimethylamine, spermidine, spermine, trimethylamine, trimethylamine, octylamine, decylamine, dioctylamine and dodecylamine, phenylene diamine, di(methylaminomethyl)phenol, tri(dimethylaminomethyl)phenol, diethylaniline, spermidine, spermine, diethylenetriamine, triethylenetetramine, tetraethylenepentamine, pentaethylenehexamine, tris(2-aminoethyl)amine and combinations thereof.

In some embodiments of the present method, the porous material is paper, polymer, foam, fabric, wood, stone, ceramic, metal, agarose gel or carbon fiber.

In some embodiments of the present method, the porous material is fiberglass paper, cotton-based paper, single-layer matrix paper or polyolefin foam pad.

In some embodiments of the present method, the porous material has an average pore size in the range of 0.1 to 100 μm.

In some embodiments of the present method, the first phase is a polymer solution, a salt solution, a non-polar solution, a micellar solution or a polyelectrolyte solution.

In some embodiments of the present method, the second phase is a polymer solution, a salt solution, a non-polar solution, a micellar solution or a polyelectrolyte solution.

In some embodiments of the present method, the volume of the first phase and the volume of the second phase are in a ratio of 1:1 to 1:1000.

In some embodiments of the present method, the nucleic acids to be purified have a size of about 20 to 1000 base pairs.

In some embodiments of the present method, the method can purify the target nucleic acids within 10 seconds to 5 minutes.

In some embodiment of the present method, the concentration of the target nucleic acids purified using the present solid-liquid phase system is 10 to 1000 folds higher than the concentration of the target nucleic acids in the nucleic acid-containing material.

In some embodiments of the present method, the nucleic acids to be purified are present in the nucleic acid-containing material at a concentration of 1 pg/mL or higher.

This invention will be better understood by reference to the examples which follow. However, one skilled in the art will readily appreciate that the examples provided are merely for illustrative purposes and are not meant to limit the scope of the invention which is defined by the claims following thereafter.

Throughout this application, it is to be noted that the transitional term "comprising", which is synonymous with "including", "containing" or "characterized by", is inclusive or open-ended, and does not exclude additional, un-recited elements or method steps.

EXAMPLES

Example 1

Preparation of Modified Porous Materials

In this example, modified porous material was prepared as follows. Spermidine was dissolved in milli-Q water to give a 5M amine aqueous solution. Four sheets of fiberglass paper, each 0.37 mm thick and with pores 2 μm in diameter, were sprayed with the prepared solution. A paper stack was made by layering the four pretreated sheets on top of each other and cutting the layered sheets into rectangles 4 cm by 0.5 cm in size. The paper stack was then washed twice with water, and dried by a lyophilizer.

Apart from spermidine, other amines may be used in the above procedure, such as trimethylamine, trimethylamine, triethylenetetramine, octylamine, decylamine, dioctylamine, dodecylamine, phenylenediamine, di(methylaminomethyl) phenol, tri(dimethylaminomethyl)phenol and diethylaniline and others.

The procedures described in this example can also be applied to modify other porous materials such as cotton-based paper, single-layer matrix paper, polyolefin foam pad and others.

Example 2

Isolation of DNA Spiked in PBS Solution Using Liquid-Solid Phase System

Paper stacks were prepared as described in Example 1. The resulting paper stacks were embedded with ATPS components as follows. An aqueous solution of ATPS components was prepared comprising 12% (w/w) PEG 400, 14.5% (w/w) $Na_2SO_4$, 2% (w/w) SDS and 0.16% (w/w) Triton-X114. The paper stacks were soaked in this solution and then dried under compressed air. Thus, ATPS components were embedded in the paper. Paper stacks embedded with ATPS components are referred to herein as ATPS-embedded paper stacks.

Figure 2:
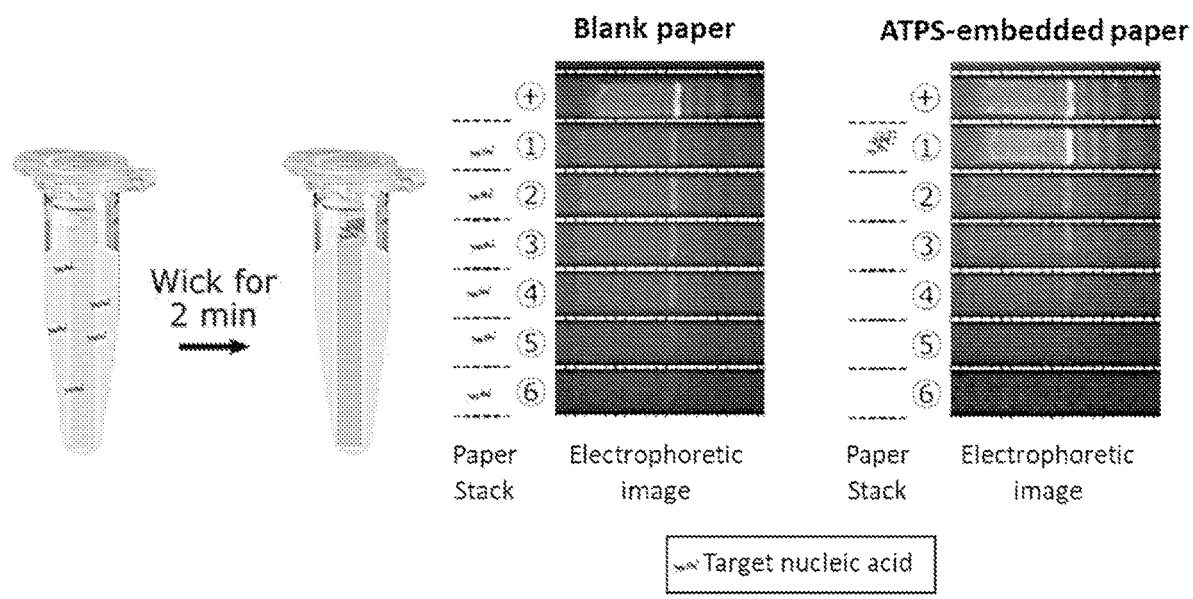
FIG. 2 shows a schematic diagram of the isolation of DNA from a solution spiked with a DNA ladder utilizing some embodiments of the present invention as described in Example 2. DNA was extracted from each of the six segments of the paper stack formed from the modified fiberglass paper. As can be seen, more DNA was extracted from the ATPS-embedded paper than from blank paper and most of the DNA was concentrated in the top segment of the ATPS-embedded paper. Fragments of all sizes present in the spiked DNA ladders were successfully extracted utilizing an embodiment of the present invention.

The ATPS-embedded paper stack and a control paper stack (made from unmodified paper that was not treated with the amine solution and without the embedded ATPS components) were then inserted into separate tubes containing a premixed DNA ladder comprising DNA fragments of 25-500 bp (INVITROGEN® 100 bp DNA Ladder) in 1×PBS with 7.5 µg/mL final DNA concentration. The paper stacks were inserted such that a section of each stack approximately 7 mm in length was not submerged in the solution (as schematically depicted in FIG. 2). The inserted paper stacks were wicked for approximately 2 minutes until the solution reached the top. As the solution of DNA in PBS traveled through the ATPS-embedded paper, the ATPS components solubilized forming ATPS. The two phases traveled through the paper stacks at different rates. It was observed that the ratio of the top and bottom phases was about 1:1. Each of the paper stacks was then divided into 6 sections approximately 7 mm in length and 5-7 µL of the solution from each of the sections was suctioned off with a pipette. DNA was precipitated by ethanol, re-suspended in Milli-Q water and analyzed by agarose gel electrophoresis. The results are depicted in FIG. 2. As can be seen, more DNA was extracted from the ATPS-embedded paper stack than from the blank paper stack, and most of the DNA was concentrated in the top segment of the ATPS-embedded paper stack. Fragments of all sizes present in the spiked DNA ladders were successfully extracted utilizing an embodiment of the present invention.

Example 3

Isolation of DNA from Blood Mimicking Mixture Using the Present Liquid-Solid Phase System Paper stacks were prepared as described in Example 1. One paper stack was embedded with ATPS components as follows. An aqueous solution of ATPS components was prepared comprising 12% (w/w) PEG 400, 14.5% (w/w) $Na_2SO_4$, 2% (w/w) SDS and 0.16% (w/w) Triton-X114. The ATPS components were embedded in the paper stacks as described in Example 2. The ATPS-embedded paper stack and a control paper stack (made from unmodified paper that was not treated with the amine solution and without the embedded ATPS components) were inserted into separate tubes (in the same way as described in Example 2) containing a premixed blood mimicking mixture comprising a buffer solution at pH 7.4 spiked with protein at the final concentration of 60-80 mg/mL and DNA ladder at the final concentration of 200 ng/mL and wicked for approximately 2 minutes until the solution reached the top. It was observed that the ratio of the top and bottom phases was about 1:1.

5-7 µL of DNA-containing solution from the top section of each paper stack approximately 7 mm in length was suctioned off with a pipette. DNA was precipitated with ethanol, re-suspended in Milli-Q water and analyzed using Nano-Drop® (Thermo Fisher Scientific, Waltham, Mass., USA; sample size for the analysis is 1 µL and Milli-Q water was used as a blank). Concentrations of protein and DNA in the original samples and the purified samples were determined spectrometrically and the yields of DNA and protein were calculated based on the actual volume of the samples. As a comparison, samples extracted using QIAamp® Circulating Nucleic Acid Kit (QIAGEN®) were also analyzed in a similar fashion. Fold change in the concentration of DNA was the ratio of DNA concentration in the purified sample to that in the original sample determined by the NanoDrop® device as described above. The results in Table 3 show that the present invention can isolate nucleic acids at a higher yield and purity as compared to the commercial kit used.

TABLE 3

Yield of DNA and protein isolated using the present invention or QIAamp ® Circulating Nucleic Acid Kit

| Test | QIAamp ® Circulating Nucleic Acid Kit | ATPS System | Control Paper |
|---|---|---|---|
| Yield of protein (%) | 24% | 16% | 87% |
| Yield of DNA (%) | 73% | 98% | 7% |
| Fold Change in Concentration of DNA | 5-fold | 10-fold | 1-fold |

Example 4

Isolation of Small DNA

A 50 bp DNA ladder and a 100 bp DNA ladder were used as small DNA sample in this example. 1 µg of the 50 bp DNA ladder and 1 µg 100 bp DNA ladder were spiked into 200 µL of 1×PBS solution to make the final concentration of 10 µg/mL. DNA was purified from the mixture using the present invention method or QIAamp® Circulating Nucleic Acid Kit (QIAGEN®). Paper stacks were prepared as described in Example 1 and embedded with ATPS components as described in Example 2. The ATPS-embedded paper stack and a control paper (made from unmodified paper that was not treated with the amine solution and without the embedded ATPS components) were inserted into separate tubes (in the same way as described in Example 2) containing the solutions with the DNA ladders and wicked for approximately 2 minutes until the solution reached the top. It was observed that the ratio of the top and bottom phases was about 1:1. The top section of each paper stack approximately 7 mm in length was cut off and 5-7 µL of the DNA-containing solution was suctioned off from that section with a pipette. DNA was precipitated by ethanol, re-suspended in Milli-Q water and analyzed by Nanodrop®. The results were compared with the result obtained by using the QIAamp® Circulating Nucleic Acid Kit (QIAGEN®).

The results in Table 4 show that the present invention can isolate small DNA at a higher yield than the commercial kit used.

TABLE 4

Isolation of small DNA fragments using the present invention or QIAamp ® Circulating Nucleic Acid Kit

| DNA | Isolation method | Yield (μg) |
| --- | --- | --- |
| 50 bp ladder | Present ATPS method | 1.82 |
| | QIAamp ® Circulating Nucleic Acid Kit | 1.5 |
| | Control stack | 0.01 |
| 100 bp ladder | Present ATPS method | 1.95 |
| | QIAamp ® Circulating Nucleic Acid Kit | 1.46 |
| | Control stack | 0.17 |

Example 5

Concentration of Circulating Cell-Free DNA (ccfDNA) in Serum

Serum samples were collected from patients and healthy individuals. ccfDNA was purified from the serum sample using the present invention or QIAamp® Circulating Nucleic Acid Kit (QIAGEN®). Paper stacks were prepared as described in Example 1 and embedded with ATPS components as described in Example 2. The ATPS-embedded paper stack and a control paper stack (made from unmodified paper that was not treated with the amine solution and without the embedded ATPS components) were inserted into separate tubes (in the same way as described in Example 2) containing the serum samples and wicked for approximately 2 minutes until the solution reached the top. It was observed that the ratio of the top and bottom phases was about 1:1 to 1:3. As compared to mimic samples used in Examples 2-4, fluctuations in the ratio of the two phases was larger when actual biological samples (e.g. serum used in this Example 5, swab samples used in Example 6 and urine) were used because there are fluctuations in concentrations of various components in individual biological samples. The top section of each paper stack approximately 7 mm in length was cut off and 5-7 μL of the DNA-containing solution was suctioned off from that section with a pipette. DNA was precipitated by ethanol, re-suspended in Milli-Q water and analyzed by NanoDrop®. The results were compared with the results obtained with QIAamp® Circulating Nucleic Acid Kit (QIAGEN®). Table 5 shows that the present invention can isolate ccfDNA from serum samples obtained from patients or healthy subjects at a higher yield than the commercial kit used.

TABLE 5

Isolation of ccfDNA from serum samples obtained from patients and healthy subjects

| DNA | Isolation method | Yield (ng) |
| --- | --- | --- |
| Patient sample | Present ATPS method | 184 |
| | QIAamp ® Circulating Nucleic Acid Kit | 89 |
| Healthy control | Present ATPS method | 27 |
| | QIAamp ® Circulating Nucleic Acid Kit | 5 |

Example 6

Isolation of Viral RNA from Buccal Swab

Buccal swab samples were self-collected by patients carrying A/H1N1 virus and by healthy subjects. Each of the swab samples was then incubated for 5 minutes in separate tubes with 500 μL, of an aqueous solution of ATPS components comprising 12% (w/w) PEG 400, 14.5% (w/w) $Na_2SO_4$, 2% (w/w) SDS and 0.16% (w/w) Triton-X114. The viral RNA was then purified from this solution using the present method or QIAamp® Circulating Nucleic Acid Kit (QIAGEN®). Paper stacks were prepared as described in Example 1 and inserted either into the solutions incubated with the swabs from patients (patient samples), the solutions incubated with the swabs from healthy subject (healthy controls), or the equal volume of PBS (negative controls), such that a section of each paper stack approximately 7 mm in length was not submerged in the solution, and wicked for approximately 2 minutes until the solution reached the top. It was observed that the ratio of the top and bottom phases was about 1:1 to 1:3. The top section of each paper stack approximately 7 mm in length was cut off and 5-7 μL of the DNA-containing solution was suctioned off from that section with a pipette. DNA was precipitated by ethanol, re-suspended in Milli-Q water and analyzed by NanoDrop®. The results were compared with the results obtained from QIAamp® Circulating Nucleic Acid Kit (QIAGEN®). Table 6 shows that the present invention can isolate viral RNA from patients or healthy subjects at a higher yield than the commercial kit used.

TABLE 6

Isolation of viral RNA from patient sample and healthy subjects

| DNA | Isolation method | Yield (ng) |
| --- | --- | --- |
| Patient sample | Present ATPS method | 160 |
| | QIAamp ® Viral RNA Mini Kit | 91 |
| Healthy control | Present ATPS method | 14 |
| | QIAamp ® Viral RNA Mini Kit | 8 |
| Negative control | Present ATPS method | 0 |
| | QIAamp ® Viral RNA Mini Kit | 0 |

What is claimed is:

1. A solid-liquid phase system for purification of nucleic acids from a nucleic acid-containing material, said system comprising a porous material and an aqueous two-phase system (ATPS), wherein the porous material comprises a surface and a plurality of pores, said surface and said pores comprising a plurality of cationic amine groups selected from the group consisting of dimethylamine, trimethylamine, octylamine, decylamine, dioctylamine, dodecylamine, phenylene diamine, di(methylaminomethyl)phenol, tri(dimethylaminomethyl)phenol, diethylaniline, spermidine, spermine, diethylenetriamine, triethylenetetramine, tetraethylenepentamine, pentaethylenehexamine, tris(2-aminoethyl) amine and combinations thereof, and wherein the aqueous two-phase system comprises a first phase and a second phase.

2. The system of claim 1, wherein the plurality of cationic amine groups is selected from the group consisting of dimethylamine, trimethylamine, octylamine, decylamine, dioctylamine, dodecylamine, phenylene diamine, di(methylaminomethyl)phenol, tri(dimethylaminomethyl)phenol, diethylaniline and combinations thereof.

3. The system of claim 1, wherein the porous material is selected from the group consisting of paper, polymer, foam, fabric, wood, stone, ceramic, metal, agarose gel and carbon fiber.

4. The system of claim 1, wherein the porous material is selected from the group consisting of fiberglass paper, cotton-based paper, single-layer matrix paper and polyolefin foam pad.

5. The system of claim 1, wherein the porous material has an average pore size in the range of 0.1 to 100 μm.

6. The system of claim 1, wherein the first phase and the second phase is independently selected from the group consisting of a polymer solution, a salt solution, a non-polar solution, a micellar solution and a polyelectrolyte solution.

7. The system of claim 1, wherein the volume of the first phase and the volume of the second phase are in a ratio of 1:1 to 1:1000.

8. The system of claim 1, wherein the nucleic acids to be purified have a size of about 20 to 1000 base pairs.

9. The system of claim 1, wherein the system can purify target nucleic acids within 10 seconds to 5 minutes.

10. The system of claim 1, wherein the concentration of purified target nucleic acids in said solid-liquid phase system is 10 to 1000 folds higher than the concentration of the target nucleic acids in the nucleic acid-containing material.

11. The system of claim 1, wherein the nucleic acids to be purified are present in the nucleic acid-containing material at a concentration of 1 pg/mL or higher.

12. A method for preparing a porous material comprising a plurality of cationic amine groups according to claim 1, comprising the steps of
(a) preparing an amine solution by dissolving the cationic amine in a buffer;
(b) soaking the porous material in the amine solution obtained from step (a);
(c) washing the porous material obtained from step (b) with water; and
(d) drying the porous material obtained from step (c), thereby obtaining the porous material comprising a plurality of cationic amine groups.

13. The method of claim 12, wherein the cationic amine of the step (a) is selected from the group consisting of dimethylamine, spermidine, spermine, trimethylamine, octylamine, decylamine, dioctylamine, dodecylamine, phenylene diamine, di(methylaminomethyl)phenol, tri(dimethylaminomethyl)phenol, diethylaniline and combinations thereof.

14. The method of claim 12, wherein the porous material is paper.

15. A method of using the solid-liquid phase system of claim 1 for rapid purification and concentration of nucleic acids from a nucleic acid-containing material.

16. A method for purifying nucleic acids from a nucleic acid-containing material, comprising the steps of:
(a) obtaining a solid-liquid phase system comprising a solid phase and a liquid phase, wherein the solid phase comprises a porous material comprising a surface and a plurality of pores, said surface and said pores comprise a plurality of cationic amine groups selected from the group consisting of dimethylamine, trimethylamine, octylamine, decylamine, dioctylamine, dodecylamine, phenylene diamine, di(methylaminomethyl)phenol, tri(dimethylaminomethyl)phenol, diethylaniline, spermidine, spermine, diethylenetriamine, triethylenetetramine, tetraethylenepentamine, pentaethylenehexamine, tris(2-aminoethyl)amine and combinations thereof, and wherein the liquid phase comprises an aqueous two-phase system (ATPS);
(b) mixing the nucleic acid-containing material with the liquid phase, thereby obtaining a mixture; and
(c) contacting the mixture obtained from step (b) with the solid phase,
wherein the nucleic acids are capable of binding to the solid phase and subsequently passing through the pores of the porous material, wherein said nucleic acids are concentrated on said porous material.

17. The method of claim 16, further comprising a step of eluting the nucleic acids from the porous material of the solid phase.

18. The method of claim 16, wherein the plurality of cationic amine groups is selected from the group consisting of dimethylamine, trimethylamine, octylamine, decylamine, dioctylamine, dodecylamine, phenylene diamine, di(methylaminomethyl)phenol, tri(dimethylaminomethyl)phenol, diethylaniline and combinations thereof.

19. The method of claim 16, wherein the porous material is selected from the group consisting of paper, polymer, foam, fabric, wood, stone, ceramic, metal, agarose gel and carbon fiber.

20. The method of claim 16, wherein the porous material is selected from the group consisting of fiberglass paper, cotton-based paper, single-layer matrix paper and polyolefin foam pad.

21. The method of claim 16, wherein the porous material has an average pore size in the range of 0.1 to 100 μm.

22. The method of claim 16, wherein the first phase and the second phase of the ATPS is independently selected from the group consisting of a polymer solution, a salt solution, a non-polar solution, a micellar solution and a polyelectrolyte solution.

23. The method of claim 16, wherein the volume of the first phase and the volume of the second phase of the ATPS are in a ratio of 1:1 to 1:1000.

24. The method of claim 16, wherein the nucleic acids to be purified have a size of about 20 to 1000 base pairs.

25. The method of claim 16, wherein the method can purify target nucleic acids within 10 seconds to 5 minutes.

26. The method of claim 16, wherein the concentration of purified target nucleic acids using said solid-liquid phase system is 10 to 1000 folds higher than the concentration of the target nucleic acids in the nucleic acid-containing material.

27. The method of claim 16, wherein the nucleic acids to be purified is present in the nucleic acid-containing material at a concentration of 1 pg/mL or higher.

28. The system of claim 1, wherein the porous material is prepared by at least the following steps:
(a) preparing an amine solution by dissolving the cationic amine in a buffer;
(b) soaking the porous material in the amine solution obtained from step (a);
(c) washing the porous material obtained from step (b) with water; and
(d) drying the porous material obtained from step (c), thereby obtaining the porous material comprising a plurality of cationic amine groups.

* * * * *